United States Patent
He et al.

(10) Patent No.: US 7,249,719 B2
(45) Date of Patent: Jul. 31, 2007

(54) METHOD AND APPARATUS FOR A MULTIPLE SOURCE VAPOR-DISPENSING DEVICE

(75) Inventors: Mengtao Pete He, Scottsdale, AZ (US); Carl Triplett, Scottsdale, AZ (US); Mary J. Conway, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 412 days.

(21) Appl. No.: 10/650,134

(22) Filed: Aug. 28, 2003

(65) Prior Publication Data

US 2004/0131509 A1   Jul. 8, 2004

Related U.S. Application Data

(60) Provisional application No. 60/407,384, filed on Aug. 30, 2002.

(51) Int. Cl.
*A61L 9/04* (2006.01)
(52) U.S. Cl. .................... 239/44; 422/123; 239/34; 239/45
(58) Field of Classification Search .......... 422/123, 422/124; 352/82; 261/30; 239/34, 44, 45
See application file for complete search history.

(56) References Cited

U.S. PATENT DOCUMENTS

| | | | |
|---|---|---|---|
| 1,397,906 A * | 11/1921 | Ruprecht | ............ 209/368 |
| 1,836,600 A | 12/1931 | Jones | |
| 2,022,394 A * | 11/1935 | Weyl | ............ 126/113 |
| 3,262,290 A | 7/1966 | Huber | |
| 3,748,438 A | 7/1973 | Costello | |
| 3,780,260 A | 12/1973 | Eisner | |
| 3,895,928 A | 7/1975 | Gonzalo | |
| 3,908,905 A | 9/1975 | Von Philipp et al. | |
| 3,923,458 A | 12/1975 | Gonzalo | |
| 3,948,445 A | 4/1976 | Andweg | |
| 4,017,030 A | 4/1977 | Coplan et al. | |
| 4,037,353 A | 7/1977 | Hennart et al. | |
| 4,084,079 A | 4/1978 | Costello | |
| 4,111,655 A | 9/1978 | Quincey | |
| 4,123,741 A | 10/1978 | Kiyono et al. | |
| 4,165,835 A | 8/1979 | Dearling | |

(Continued)

FOREIGN PATENT DOCUMENTS

DE   35 35 564   5/1986

(Continued)

OTHER PUBLICATIONS

PCT International Search Report issued Dec. 17, 2003 for International Application No. PCT/US03/26511, International Filing Date Aug. 26, 2003, 4 pages.

(Continued)

*Primary Examiner*—Gladys J P Corcoran
*Assistant Examiner*—Sean E. Conley
(74) *Attorney, Agent, or Firm*—Snell & Wilmer LLP

(57) ABSTRACT

A vapor-dispensing device that, through a delivery system, facilitates evaporation of multiple volatizable materials into an environment. In one embodiment, a common evaporative region is utilized; in another, a controller suitably controls an aspect or characteristic of the evaporation.

4 Claims, 3 Drawing Sheets

U.S. PATENT DOCUMENTS

| | | |
|---|---|---|
| 4,171,340 A | 10/1979 | Nishimura et al. |
| 4,208,012 A | 6/1980 | Dutcher |
| 4,214,146 A | 7/1980 | Schimanski |
| 4,220,281 A | 9/1980 | Martens, III et al. |
| 4,228,124 A | 10/1980 | Kashihara et al. |
| 4,242,969 A | 1/1981 | Steigerwald et al. |
| 4,293,173 A | 10/1981 | Tricca |
| 4,294,778 A | 10/1981 | DeLuca |
| 4,346,059 A | 8/1982 | Spector |
| 4,391,781 A | 7/1983 | Van Lit |
| 4,408,813 A | 10/1983 | Koehler |
| 4,413,779 A | 11/1983 | Santini |
| 4,415,797 A | 11/1983 | Choustoulakis |
| 4,425,302 A | 1/1984 | Pons Pons |
| 4,467,117 A | 8/1984 | Zobele |
| 4,518,212 A | 5/1985 | Rumble |
| 4,530,556 A | 7/1985 | Bonus |
| 4,537,351 A | 8/1985 | Wilson |
| 4,544,592 A | 10/1985 | Spector |
| 4,549,250 A | 10/1985 | Spector |
| 4,556,539 A | 12/1985 | Spector |
| 4,571,485 A | 2/1986 | Spector |
| 4,574,181 A | 3/1986 | Spector |
| 4,595,564 A | 6/1986 | Spector et al. |
| 4,631,387 A | 12/1986 | Glucksman |
| 4,658,985 A | 4/1987 | Madsen et al. |
| 4,660,764 A | 4/1987 | Joyaux et al. |
| 4,662,679 A | 5/1987 | Franck |
| 4,675,504 A | 6/1987 | Suhajda |
| 4,686,353 A | 8/1987 | Spector |
| 4,695,434 A | 9/1987 | Spector |
| 4,703,155 A | 10/1987 | Suhajda |
| 4,707,336 A | 11/1987 | Jones |
| 4,714,984 A | 12/1987 | Spector |
| 4,718,856 A | 1/1988 | Pinkerton et al. |
| 4,725,712 A | 2/1988 | Schroeder |
| 4,731,520 A | 3/1988 | Glucksman |
| 4,731,522 A | 3/1988 | Manchester |
| 4,732,321 A | 3/1988 | Dolan |
| 4,734,560 A | 3/1988 | Bowen |
| 4,739,928 A | 4/1988 | O'Neil |
| 4,743,406 A | 5/1988 | Steiner et al. |
| 4,753,389 A | 6/1988 | Davis |
| 4,777,345 A | 10/1988 | Manchester |
| 4,780,286 A | 10/1988 | Parent et al. |
| 4,795,883 A | 1/1989 | Glucksman et al. |
| 4,798,935 A | 1/1989 | Pezaris |
| 4,800,239 A | 1/1989 | Hill |
| 4,801,271 A | 1/1989 | Piper |
| 4,804,821 A | 2/1989 | Glucksman |
| 4,808,347 A | 2/1989 | Dawn |
| 4,816,973 A | 3/1989 | Atalla et al. |
| 4,830,791 A | 5/1989 | Muderlak et al. |
| 4,837,421 A | 6/1989 | Luthy |
| 4,849,606 A | 7/1989 | Martens, III et al. |
| 4,853,517 A | 8/1989 | Bowen et al. |
| 4,878,615 A | 11/1989 | Losi |
| 4,886,469 A | 12/1989 | Jseng |
| 4,915,301 A | 4/1990 | Munteanu |
| 4,919,981 A | 4/1990 | Levey et al. |
| 4,931,224 A | 6/1990 | Holzner, Sr. |
| 4,931,258 A | 6/1990 | Zlotnik et al. |
| 4,968,456 A | 11/1990 | Muderlak et al. |
| D315,789 S | 3/1991 | Muderlak |
| 4,998,671 A | 3/1991 | Leifheit |
| 5,004,435 A | 4/1991 | Jammet |
| 5,014,913 A | 5/1991 | Hoyt et al. |
| 5,015,442 A | 5/1991 | Hirai |
| 5,029,729 A | 7/1991 | Madsen et al. |
| 5,038,394 A | 8/1991 | Hasegawa et al. |
| 5,050,798 A | 9/1991 | Sullivan |
| 5,106,317 A | 4/1992 | Taylor |
| 5,111,477 A | 5/1992 | Muderlak |
| 5,115,975 A | 5/1992 | Shilling |
| 5,121,881 A | 6/1992 | Lembeck |
| 5,126,078 A | 6/1992 | Steiner et al. |
| 5,136,684 A | 8/1992 | Lonker et al. |
| 5,147,582 A | 9/1992 | Holzner, Sr. et al. |
| 5,148,984 A | 9/1992 | Bryson, Jr. et al. |
| 5,175,791 A | 12/1992 | Muderlak et al. |
| 5,196,171 A | 3/1993 | Peltier |
| 5,201,025 A | 4/1993 | Landesberg |
| 5,217,696 A | 6/1993 | Wolverton et al. |
| 5,220,636 A | 6/1993 | Chang |
| 5,222,186 A | 6/1993 | Schimanski et al. |
| 5,223,182 A | 6/1993 | Steiner et al. |
| 5,233,680 A | 8/1993 | Fussell |
| 5,239,610 A | 8/1993 | Shao |
| 5,240,426 A | 8/1993 | Barla |
| 5,285,014 A | 2/1994 | Gilchrist |
| 5,290,546 A | 3/1994 | Hasegawa et al. |
| 5,295,845 A | 3/1994 | Changxing |
| 5,314,669 A | 5/1994 | Hamilton |
| 5,320,542 A | 6/1994 | Cheng |
| 5,339,065 A | 8/1994 | Slenker |
| 5,342,584 A | 8/1994 | Fritz et al. |
| 5,373,581 A | 12/1994 | Smith |
| 5,375,728 A | 12/1994 | West |
| 5,376,338 A | 12/1994 | Zlotnik |
| 5,382,410 A | 1/1995 | Peltier |
| D355,251 S | 2/1995 | Paulovich et al. |
| 5,394,506 A | 2/1995 | Stein et al. |
| 5,402,517 A | 3/1995 | Gillett et al. |
| D357,330 S | 4/1995 | Wong et al. |
| 5,431,859 A | 7/1995 | Tobin |
| 5,431,885 A | 7/1995 | Zlotnik et al. |
| 5,445,802 A | 8/1995 | Wendelken |
| 5,465,198 A | 11/1995 | Kellogg |
| 5,480,591 A | 1/1996 | Lagneaux et al. |
| 5,481,442 A | 1/1996 | Wiltshire et al. |
| 5,484,086 A | 1/1996 | Pu |
| 5,498,397 A | 3/1996 | Horng |
| 5,521,357 A | 5/1996 | Lock et al. |
| 5,522,008 A | 5/1996 | Bernard |
| 5,547,616 A | 8/1996 | Dancs et al. |
| 5,556,192 A | 9/1996 | Wang |
| 5,567,361 A | 10/1996 | Harper |
| 5,574,821 A | 11/1996 | Babasade |
| 5,575,992 A | 11/1996 | Kunze |
| 5,577,156 A | 11/1996 | Costello |
| 5,591,395 A | 1/1997 | Schroeder et al. |
| 5,624,230 A | 4/1997 | Taylor et al. |
| 5,634,806 A | 6/1997 | Hahn |
| 5,647,052 A | 7/1997 | Patel et al. |
| 5,647,053 A | 7/1997 | Schroeder et al. |
| 5,651,942 A | 7/1997 | Christinsen |
| 5,662,835 A | 9/1997 | Collingwood |
| 5,664,958 A | 9/1997 | Chadwick et al. |
| 5,700,430 A | 12/1997 | Bonnema et al. |
| 5,735,460 A | 4/1998 | Eisenbraun |
| 5,749,520 A | 5/1998 | Martin et al. |
| 5,750,498 A | 5/1998 | Soeda et al. |
| 5,765,751 A | 6/1998 | Joshi |
| 5,788,155 A | 8/1998 | Martin et al. |
| 5,788,931 A | 8/1998 | Munoz Quintana |
| 5,796,914 A | 8/1998 | Gatzemeyer et al. |
| 5,805,768 A | 9/1998 | Schwartz et al. |
| 5,810,265 A | 9/1998 | Cornelius et al. |
| 5,813,873 A | 9/1998 | McBain et al. |
| 5,832,648 A | 11/1998 | Malone |
| 5,873,529 A | 2/1999 | Johnson |
| 5,875,968 A | 3/1999 | Miller et al. |
| 5,884,808 A | 3/1999 | Muderlak et al. |
| 5,899,381 A | 5/1999 | Gordon et al. |

| | | |
|---|---|---|
| 5,903,710 A | 5/1999 | Wefler et al. |
| 5,926,614 A | 7/1999 | Steinel |
| 5,928,605 A | 7/1999 | Bonnema et al. |
| 5,932,204 A | 8/1999 | Joshi |
| 5,937,140 A | 8/1999 | Leonard et al. |
| 5,940,577 A | 8/1999 | Steinel |
| 5,944,223 A | 8/1999 | Klima et al. |
| 5,945,094 A | 8/1999 | Martin et al. |
| 5,955,701 A | 9/1999 | Schockner et al. |
| 5,957,701 A | 9/1999 | McMillin |
| 5,970,643 A | 10/1999 | Gawel, Jr. |
| 5,976,503 A | 11/1999 | Martin et al. |
| 5,998,735 A | 12/1999 | Patterson, Jr. |
| 6,021,254 A | 2/2000 | Hunter |
| 6,031,967 A | 2/2000 | Flashinski et al. |
| 6,032,930 A | 3/2000 | Calino |
| 6,036,536 A | 3/2000 | Chiu |
| 6,044,202 A | 3/2000 | Junkel |
| 6,045,374 A | 4/2000 | Candeloro |
| 6,050,551 A | 4/2000 | Anderson |
| 6,051,788 A | 4/2000 | Nichols |
| 6,078,728 A | 6/2000 | O'Rourke et al. |
| 6,085,026 A | 7/2000 | Hammons et al. |
| 6,097,881 A | 8/2000 | DeWitt et al. |
| 6,099,137 A | 8/2000 | McCormick et al. |
| 6,101,315 A | 8/2000 | Steinel, Jr. |
| 6,104,866 A | 8/2000 | DeWitt et al. |
| 6,104,867 A | 8/2000 | Stathakis et al. |
| D430,659 S | 9/2000 | Zaraboza et al. |
| 6,123,935 A | 9/2000 | Wefler et al. |
| 6,141,496 A | 10/2000 | Sundberg et al. |
| 6,148,143 A | 11/2000 | Steinel, Jr. |
| 6,156,088 A | 12/2000 | Cardarelli |
| 6,169,595 B1 * | 1/2001 | Manne ........................ 352/85 |
| 6,197,262 B1 | 3/2001 | Del Ben |
| 6,197,263 B1 | 3/2001 | Blount |
| 6,227,118 B1 | 5/2001 | Nance |
| 6,236,807 B1 | 5/2001 | Ruffolo et al. |
| 6,249,645 B1 | 6/2001 | Smith |
| 6,254,065 B1 | 7/2001 | Ehrensperger et al. |
| 6,264,548 B1 | 7/2001 | Payne, Jr. et al. |
| 6,269,979 B1 | 8/2001 | Dumont |
| 6,270,720 B1 | 8/2001 | Mandish |
| 6,275,651 B1 | 8/2001 | Voit |
| 6,278,840 B1 | 8/2001 | Basaganas Millan |
| 6,285,830 B1 | 9/2001 | Basaganas Millan |
| 6,289,176 B1 | 9/2001 | Martter et al. |
| 6,302,559 B1 | 10/2001 | Warren |
| 6,315,959 B2 | 11/2001 | Mandish |
| 6,328,791 B1 | 12/2001 | Pillion et al. |
| 6,342,676 B1 | 1/2002 | Ha |
| 6,349,168 B1 | 2/2002 | Jaworski |
| 6,352,210 B1 | 3/2002 | Requejo |
| 6,354,513 B1 | 3/2002 | Basaganas Millan |
| 6,361,752 B1 | 3/2002 | Demarest et al. |
| 6,364,673 B1 | 4/2002 | Lee |
| 6,368,564 B1 | 4/2002 | Smith |
| 6,371,815 B1 | 4/2002 | Wetzel et al. |
| 6,374,044 B1 | 4/2002 | Freidel |
| 6,374,045 B2 | 4/2002 | Basaganas Millan |
| 6,381,408 B1 | 4/2002 | Jaworski et al. |
| 6,487,367 B2 * | 11/2002 | Vieira ........................ 392/395 |
| 6,603,924 B2 | 8/2003 | Brown et al. |
| 6,714,725 B2 | 3/2004 | Grone et al. |
| 6,842,218 B1 * | 1/2005 | Manne ........................ 352/85 |
| 2001/0031225 A1 | 10/2001 | Mandish |
| 2001/0053283 A1 | 12/2001 | Levine et al. |
| 2002/0144992 A1 | 10/2002 | Vieira |
| 2003/0138241 A1 | 7/2003 | Ambrosi et al. |

FOREIGN PATENT DOCUMENTS

| | | |
|---|---|---|
| DE | 41 31 613 | 3/1993 |
| EP | 0 296 807 | 12/1988 |
| EP | 0 669 137 | 8/1995 |
| EP | 0 911 041 | 4/1999 |
| GB | 402507 | 12/1933 |
| GB | 2 356 815 | 6/2001 |
| WO | WO 00 76292 | 12/2000 |
| WO | WO 01 10739 | 2/2001 |
| WO | WO 01/68154 | 9/2001 |
| WO | WO 01/93919 | 12/2001 |

OTHER PUBLICATIONS

PCT International Search Report issued Apr. 21, 2004 for International Application No. PCT/US03/26754, International Filing Date Aug. 28, 2003, 4 pages.

PCT International Search Report issued Nov. 12, 2003 for International Application No. PCT/US03/25245, International Filing Date Aug. 13, 2003, 4 pages.

PCT International Search Report issued Oct. 7, 2003 for International Application No. PCT/US03/04082, International Filing Date Feb. 12, 2003, 8 pages.

PCT International Search Report issued Dec. 16, 2003 for International Application No. PCT/US03/25244, International Filing Date Aug. 13, 2003, 3 pages.

PCT International Search Report issued Dec. 16, 2003 for International Application No. PCT/US03/25246, International Filing Date Aug. 13, 2003, 3 pages.

PCT International Search Report issued Dec. 19, 2003 for International Application No. PCT/US03/25243, International Filing Date Aug. 13, 2003, 4 pages.

Brochure—"Decora Devices," by Leviton, date unknown, Section A, pp. A1-A36.

* cited by examiner

METHOD AND APPARATUS FOR A MULTIPLE SOURCE VAPOR-DISPENSING DEVICE

CROSS-REFERENCE TO RELATED APPLICATIONS

This application claims priority to U.S. Provisional Patent Application Ser. No. 60/407,384 entitled "Method and Apparatus for a Multiple Source Vapor-Dispensing Device," filed Aug. 30, 2002, and is incorporated herein by reference.

FIELD OF INVENTION

This invention relates, generally, to vapor-dispensing devices and, in particular, to a vapor-dispensing device that facilitates evaporation of multiple volatizable materials into an environment.

BACKGROUND OF THE INVENTION

Indoor air fresheners consisting of a source of fragrant material and a dispersion system for projecting material vapor into the air have been used for many years. Liquids, solids, and gels have been used as material sources. Dispersion systems also have included evaporation regions such as the surface of a gelatinous material source or, as in U.S. Pat. No. 4,919,981, the leaf or center of a decorative artificial flower. Many of these systems have included a cover, such as for use in connection with a gelatinous air freshener, which can be raised and lowered to affect the amount of fragrant vapor released.

Notwithstanding these existing devises and systems, there is a long-felt and so far unsatisfied need, however, for an indoor vapor dispensing device such as an air freshening system which allows more than one source of fragrant material to be dispersed into the environment from a single device. The need for a device that permits the user to control the release of the materials without undue physical manipulation of the device is particularly acute.

SUMMARY OF THE INVENTION

The present invention provides a vapor-dispensing device that, through a delivery system, facilitates evaporation of multiple volatizable materials from an evaporation region into an environment.

In accordance with one embodiment the evaporation region comprises a single region through which two or more volatizable materials may pass into the environment. In accordance with another embodiment a controller is employed to facilitate controlled delivery of the two or more volatizable materials into the environment

BRIEF DESCRIPTION OF THE DRAWING

The subject invention will hereinafter be described in conjunction with the appended drawing figures, wherein like numerals denote like elements, and.

DETAILED DESCRIPTION

Systems and methods in accordance with the present invention generally provide for a vapor-dispensing device that, through a delivery system, facilitates evaporation of multiple volatizable materials into an environment.

Figure 1:
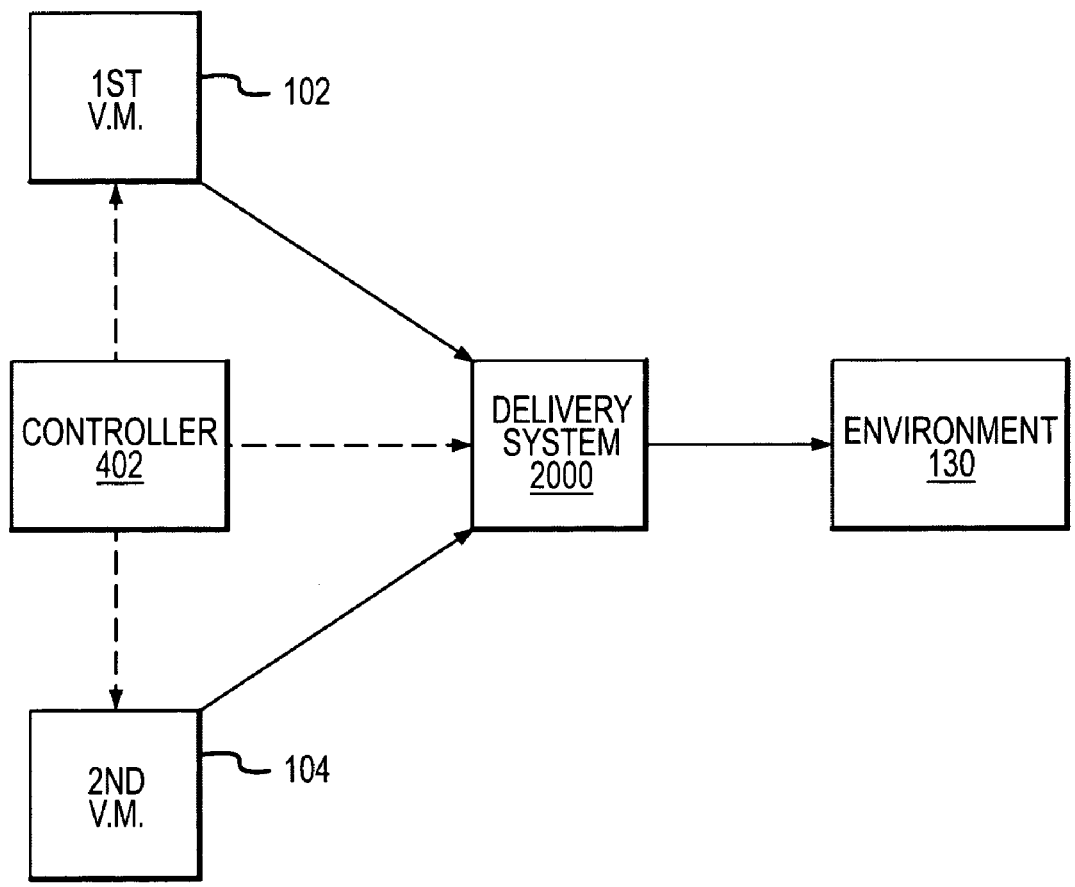
FIG. 1 is a schematic overview of a system providing a context in which the present invention may be practiced.

Referring to FIG. 1, a vapor-dispensing device in accordance with the present invention generally comprises a delivery system 2000 communicating with a first volatizable material 102, a second volatizable material 104, a controller 402, and an environment 130.

Volatizable materials 102 and 104 generally comprise any material which may vaporize. More specifically, volatizable materials 102 and 104 may comprise one or more suitable liquids, waxes, colloids, gels, solids, or other form of matter which may be caused to evaporate, sublimate, or otherwise transformed to a vapor. For example, volatizable materials 102 and 104 may each comprise one or more different natural or synthetic oil bearing fragrances, such as floral, citrus, exotic spices, and the like. But any material which may be volatized into an environment, whether now known or hereinafter devised, may be used in the present invention.

For example, materials 102 and 104 may comprise fragrance containing materials, insecticides or other materials. In accordance with various aspects of the present invention, the volatizable materials can be any number of conventional materials dispensed from vapor dispensers including fragrances, disinfectants, sanitizing agents, insect repellants, insecticides and the like. Preferably, and in accordance with a preferred aspect of the present invention, at least one of materials 102 and 104 comprises a fragrance material and system 2000 is used as a air freshening device.

In certain applications, various combinations of materials may be desirable. For example, material 102 may comprise one fragrance, for example, a strawberry fragrance containing material, and material 104 may comprise another complimentary fragrance, for example, a crème fragrance containing material. Alternatively, material 104 may comprise another material, for example, an insecticide or other material. Of course, various combinations of materials may be employed in connection with the various embodiments of the present invention.

Volatizable materials 102 and 104 may be attached to the delivery system 2000 or otherwise contained or maintained in position to suitably communicate with the delivery system 2000 by any method now known or hereinafter devised. Also, volatizable materials 102 and 104 may be physically separated from, or in the alternative, maintained in physical contact with one another. Where the volatizable materials 102 and 104 are physically separated, the separation can be accomplished with a suitable boundary such as a common wall, or the separation can be accomplished by means of containers. For example, containers such as reservoirs, bottles, or other such containers may be used to separate volatizable materials 102 and 104. While FIG. 2 demonstrates one embodiment of volatizable materials 102 and 104, any structure capable of separating these volatizable materials, where desired, whether now known or hereinafter devised, may be used in the present invention.

Controller 402 can be any device which suitably enables some level of control of the way in which, the amount of, or any other characteristic relating to the release of materials 102 and 104 into the environment. For example, in accordance with one embodiment, controller 402 may be operable to adjust the relative or absolute amounts of volatizable materials 102 and 104 released into the environment 130 at rates preferred by the user. In accordance with another embodiment, controller 402 may be suitably configured to enable alternative, or other modified actuation of system 2000 to facilitate release of materials 102 and 104. For example, controller 402 may use one or more types of power, including electrical, mechanical, heat, or other sources or combinations of sources. Controller 402 may, for example, comprise a heating element that is selectively controlled to facilitate selective volatization of materials 102 and 104.

Inasmuch as the operation of liquid vaporizers is generally known to those of skill in the art, the operation will not be described in detail herein. Suffice it to say, however, that in accordance with various aspects of a preferred embodiment of the present invention, system 2000 may be plugged into a conventional electrical outlet thereby causing a heater unit (not shown) to heat materials 102 and 104, perhaps via transfer mechanism 110 discussed in greater detail hereinbelow, to permit the vaporized liquid which has been drawn up into transfer mechanism 110 and allow the same to escape from system 2000. The term "vaporized" as used herein is used in a conventional sense and is intended to include not only the formation of vapors but also the formation of small aerosol sized particles which, as is known in the art, may be generated by actuation of such device. While any heater unit may be used, preferably the heating unit comprises a heating element which can be readily and reliably charged through use in a conventional outlet.

Controller 402 may communicate with volatizable materials 102 and 104 or delivery system 2000, or any of their components or subcomponents, in any combination. However, in general, controller 402 either permits vaporization, controls the rate or timing of vaporization or otherwise impacts a characteristic of vaporization.

For example, in the aforementioned illustrative example where material 102 comprises a fragrance containing material and material 104 is some other vaporizable material, e.g., an insecticide, controller 402 may permit sequential and/or intermittent actuation. For example, in one case, controller 402 may permit substantially constant vaporization of fragrance material 102 and intermittent vaporization of insecticide material 104. However, various other operation modes may be employed.

Environment 130 corresponds to any defined space, whether open or enclosed by one or more surfaces, walls, ceilings, floors, or other solid or fictitious boundaries, which receives the evaporated material. For example, environment 130 may correspond to a residential room (bedroom, bathroom, kitchen, etc.), commercial space (factory floor, office cubicles, etc.), automotive enclosure (car, truck, recreational vehicle), airline compartment, or any other space in which it is desirable to deliver a vapor.

Figure 2:
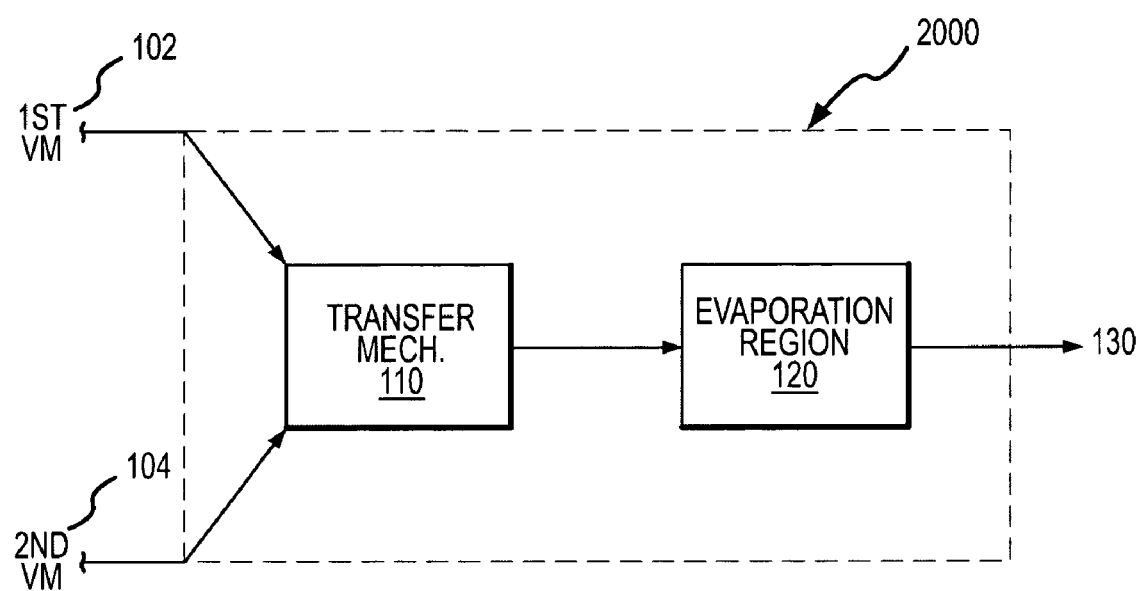
FIG. 2 is a schematic view of exemplary a vapor-dispensing device in accordance with the present invention; and, FIG. 3 is a schematic view of a further exemplary vapor dispensing device.

As shown on FIG. 2, delivery system 2000 generally comprises a transfer mechanism 110 and an evaporation region 120.

Transfer mechanism 110 preferably comprises any component or combination of components configured to communicate with both the first and second volatizable materials and the evaporation region. More specifically, transfer mechanism 110 may comprise one or more devices which may be caused to deliver volatizable materials 102 and 104 to evaporation region 120. Transfer mechanism 110 may, but need not, be contiguous with or physically attached to volatizable materials 102 and 104 or contiguous with or fastened to evaporation region 120. However, in general, transfer mechanism facilitates transport of materials 102 and 104 to environment 130, preferably through evaporation region 120.

Figure 3:
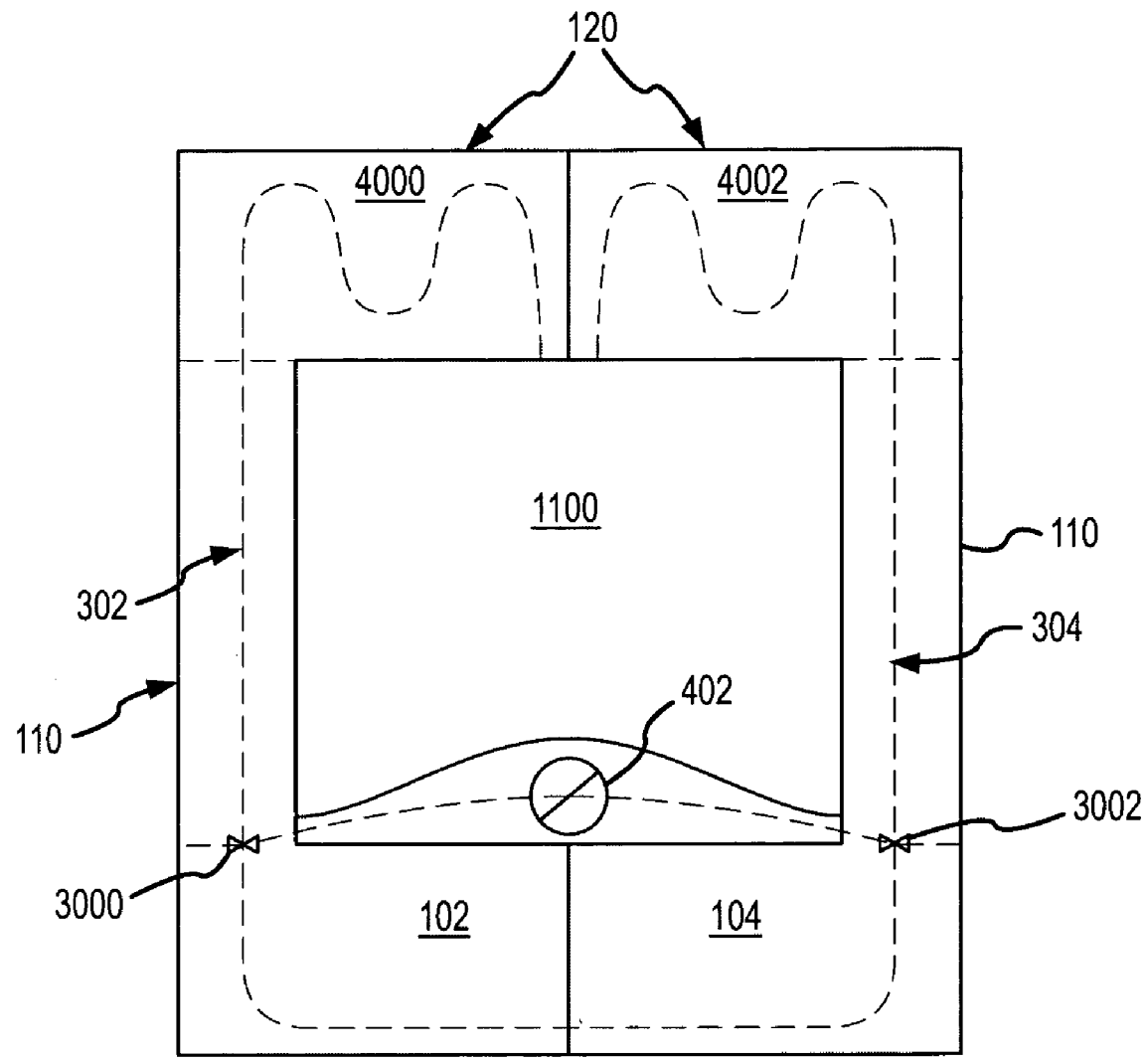

With reference now to FIG. 3, an exemplary embodiment of transfer mechanism 110, may suitably comprise a first wick structure 302 and a second wick structure 304. Preferably, wick structures 302 and 304 operatively communicate with volatizable materials 102 and 104 and evaporation region 120. That is, wick structures 302 and 304 may be contiguous with, attached to, or otherwise in operative communication with volatizable materials 102 and 104. Similarly, wick structures 302 and 304 may be contiguous with, attached to, or otherwise in operative communication with evaporation region 120. As shown, transfer mechanism 110 may be configured with an open area 1100 between two separate sides of the transfer mechanism 110; specifically, wick structures 302 and 304. In this embodiment, as also shown, volatizable materials 102 and 104 suitably comprise liquid materials held in separate containers and delivered through wick structures 302 and 304, respectively, to evaporation region 120 (described below), and thence to environment 130.

While FIG. 3 shows an exemplary embodiment of transfer mechanism 110, any transfer mechanism capable of communicating with both volatizable materials 102 and 104 and evaporation region 120, whether now known or hereinafter devised, may be used in the present invention. In this regard, transfer mechanism may comprise suitable wick materials including porous/sintered plastics such as high density polyethylene and polypropylene, bonded fibers, glass sintered fibers, ceramic materials, carbon fibers, sintered carbon, wood, compressed wood composites bundled or woven material fibers, bundled or manmade fibers. In general, the desired transfer material can be formed of any suitable material now known or hereafter devised by those skilled in the art.

Referring again to FIG. 2, evaporation region 120 preferably comprises any suitable component or combination of components configured to facilitate evaporation of materials from delivery system 2000 into environment 130. Evaporation region 120 may be attached to delivery system 2000 or otherwise contained or maintained in position to communicate with delivery system 2000. Evaporation region 120 may or may not comprise the same material comprising transfer mechanism 110.

More specifically, referring now to FIG. 3, evaporation region 120 may comprise pads 4000 and 4002, which may be respectively caused to receive volatizable materials 102 and 104 from wick structures 302 and 304 and to release volatizable materials 102 and 104 into the environment, such as by actuation of controller 402. In accordance with an exemplary embodiment of the present invention, pads 4000, 4002 comprise any material that enables the evaporation of volatizable material therefrom. For example, such materials may include porous/sintered plastics such as high density polyethylene and polypropylene, bonded fibers, glass sintered fibers, ceramic materials, carbon fibers, sintered carbon, wood, compressed wood composites bundled or woven material fibers, bundled or manmade fibers, combinations thereof and/or the like. Further, pads 4000, 4002 may be arranged in any suitable manner using any variety of suitable means that maintains the positioning of the materials relative to each other and does not adversely affect travel of liquid through the material. In general, pads 4000, 4002 employ capillary action to draw volatizable materials 102 and 104 from transfer mechanism 110 and expose material to environment 130 for evaporative release.

Although the exemplary embodiment of FIG. 3 shows two pads, one or more pads may be used. Pads 4000 and 4002 may, but need not, comprise the same material. Moreover, pads 4000 and 4002 may be shaped in one or more shapes, such as rectangular, elliptical, square, triangular, or any other arbitrary rectilinear or curvilinear shape. Also, pads 4000 and 4002 may, but need not, be physically attached to transfer mechanism 110. FIG. 3, for example, shows an embodiment of the present invention in which pads 4000 and 4002 are respectively attached to wick structures 302 and 304, which in turn are respectively attached to volatizable materials 102 and 104.

While FIG. 3 shows one embodiment of evaporation region 120, any structure of any configuration which facilitates the receipt and release of volatizable materials 102 and 104 into environment 130, whether now known or hereinafter devised, may be used in the present invention.

FIG. 3's exemplary embodiment includes controller 402 manipulated manually by the user. Using any suitable conventional electric signal technology controller 402 communicates the user's manual input to the transfer mechanism 110 so as to control the absolute and relative amounts of volatizable materials 102 and 104 from evaporation region 120. Specifically, in this embodiment, transfer mechanism 110 comprises wick structures 302 and 304 which are connected to valves 3000 and 3002. Controller 402 communicates with valves 3000 and 3002 to control the amounts of volatizable materials 102 and 104 reaching evaporation region 120, and thus the amounts released into the environment.

In another embodiment of the present invention, wick structures 302 and 304 include conventional filament structures which receive signals from controller 402. The filament structures act to alter heat levels in wick structures 302 and 304, thereby controlling the amounts of volatizable materials 102 and 104 reaching evaporation region 120. Alternatively, and in addition, filament structures may be located in volatizable materials 102 and 104, evaporation region 120, or both.

For the sake of brevity, conventional electrical and mechanical design techniques used in developing various vapor-dispensing devices (and the various components thereof) are not described in detail herein. The devices disclosed herein may be configured through application of general electrical and mechanical principles. Although the embodiments described herein show vapor-dispensing devices that are generally quadrilateral in shape, other design styles could be formulated. Vapor dispensing devices could be readily formulated with angular, round, oval or other shapes, for example, as well as with combinations of multiple shapes and structures. In a further embodiment, the vapor-dispensing device may be adorned with an ornamental design such as a floral design, an outdoor scene, a cartoon or movie character, or the like.

The particular implementations shown and described herein are examples of the present invention and are not intended to otherwise limit the scope of the present invention in any way. It should be noted that many alternative or additional components or features may be added without departing from the invention this described.

We claim:

1. A vapor-dispensing device comprising:
    a container containing at least two volatizable materials;
    a first volatizable material contained in said container;
    a second volatizable material contained in said container and separately contained from said first volatizable material; and
    a common delivery system comprising a transfer mechanism and an evaporation region, said transfer mechanism comprising a first wick structure in liquid communication with said first volatizable material and a second wick structure in liquid communication with said second volatizable material, said evaporation region comprising a pad in liquid communication with said first wick structure and said second wick structure, wherein said evaporation region is configured to facilitate evaporation of said first volatizable material and said second volatizable material into an environment; and
    a controller configured to modulate the amounts of said first and second volatizable materials available to said first wick structure and said second wick structure.

2. The vapor-dispensing device of claim 1, wherein said first volatizable material includes a first fragrance and said second volatizable material includes a second fragrance.

3. The vapor dispensing device of claim 1, wherein said first and second volatizable materials are physically attached to said delivery system.

4. The vapor-dispensing device of claim 1, wherein said transfer mechanism is physically attached to said delivery system.

* * * * *